(12) United States Patent
De Vries et al.

(10) Patent No.: US 9,326,594 B2
(45) Date of Patent: *May 3, 2016

(54) POSITION SENSING TOOTHBRUSH

(71) Applicant: KONINKLIJKE PHILIPS N.V., Eindhoven (NL)

(72) Inventors: Johannes Hotze Bernhard De Vries, Haren (NL); Evert Alle Helfrich, Seattle, WA (US); Pieter Johannes Bax, Drachten (NL); Chad Brinckerhoff, Issaquah, WA (US); Sandor Gordijn, Mierlo (NL); Theo Anjes Maria Ruijl, Oirschot (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/695,221

(22) Filed: Apr. 24, 2015

(65) Prior Publication Data

US 2015/0230594 A1    Aug. 20, 2015

Related U.S. Application Data

(62) Division of application No. 14/097,994, filed on Dec. 5, 2013, now Pat. No. 9,049,920, which is a division of application No. 13/516,447, filed as application No. PCT/IB2010/055333 on Nov. 22, 2010, now abandoned.

(60) Provisional application No. 61/289,476, filed on Dec. 23, 2009.

(51) Int. Cl.
*A61C 17/22* (2006.01)
*A46B 15/00* (2006.01)
*A46B 9/04* (2006.01)

(52) U.S. Cl.
CPC .............. *A46B 15/0002* (2013.01); *A46B 9/04* (2013.01); *A46B 15/0006* (2013.01);

(Continued)

(58) Field of Classification Search
CPC ............ A46B 15/0002; A46B 15/0004; A46B 15/0008; A46B 15/0014; A46B 15/0038; A61C 17/00
USPC .................... 15/22.1, 105, 167.1; 433/72, 75
See application file for complete search history.

(56) References Cited

U.S. PATENT DOCUMENTS 5,876,207 A  * 3/1999  Sundius et al. ............... 433/216
6,536,068 B1    3/2003  Yang et al.

(Continued)

FOREIGN PATENT DOCUMENTS

DE    202004002204       3/2005
JP    2002223854 A       8/2002

(Continued)

OTHER PUBLICATIONS

Lee et al: "Development of Smart Toothbrush Monitoring System for Ubiquitous Healthcare"; Conference Proceedings IEEE Eng Med Biol Soc. 2006, vol. 1, pp. 6422-6425.

(Continued)

*Primary Examiner* — Michael Jennings

(57) ABSTRACT

The toothbrush includes a handle portion (12 or 55) and a brushhead portion (14 or 57) with a bristle set (20 or 53) at one end of the brushhead. At least one sensor (16 or 56 is located either on the handle of the toothbrush or on the bristle set back plate (54) of the toothbrush. When the sensor is located on the handle of the toothbrush, the position of the brushhead is determined by a processor (44 or 58) relative to the inside or outside surfaces of the teeth on the basis of the temperature detected by the sensor, either the outside environmental temperature or the skin temperature of the user. When the sensor is located on the bristle set back plate, the determination is made on the basis of the position of the bristle set relative to the cheek of the user.

7 Claims, 6 Drawing Sheets

(52) U.S. Cl.
CPC ........ *A46B 15/0008* (2013.01); *A46B 15/0014* (2013.01); *A46B 15/0038* (2013.01); *A46B 15/0044* (2013.01); *A61C 17/221* (2013.01); *A46B 15/0004* (2013.01)

(56) References Cited

U.S. PATENT DOCUMENTS

| | | | |
|---|---|---|---|
| 6,731,213 | B1 | 5/2004 | Smith |
| 6,786,732 | B2 | 9/2004 | Savill et al. |
| 7,596,827 | B1 | 10/2009 | Puneet |
| 7,917,986 | B2 | 4/2011 | Jiminez et al. |
| 7,965,571 | B2 * | 6/2011 | Jeong et al. ............ 365/222 |
| 7,976,388 | B2 * | 7/2011 | Park et al. ............... 463/37 |
| 8,137,109 | B2 * | 3/2012 | Gatzemeyer et al. ......... 434/238 |
| 8,261,399 | B2 | 9/2012 | Wu et al. |
| 8,337,213 | B2 * | 12/2012 | Puurunen et al. ............ 434/263 |
| 8,351,299 | B2 * | 1/2013 | Cohen et al. ............... 368/10 |
| 2002/0133308 | A1 | 9/2002 | Lundell et al. |
| 2006/0194164 | A1 * | 8/2006 | Altshuler et al. ............ 433/29 |
| 2007/0270221 | A1 * | 11/2007 | Park et al. ............... 463/37 |
| 2008/0060148 | A1 | 3/2008 | Pinyayev et al. |
| 2008/0102953 | A1 * | 5/2008 | Schultz ............... 463/37 |
| 2009/0083924 | A1 | 4/2009 | Shepherd et al. |
| 2009/0092955 | A1 * | 4/2009 | Hwang ............... 434/263 |
| 2009/0241278 | A1 | 10/2009 | Lemchen |
| 2009/0307859 | A1 * | 12/2009 | Mottram et al. ............ 15/105 |
| 2010/0043157 | A1 * | 2/2010 | Jungnickel et al. ............ 15/22.1 |
| 2010/0043161 | A1 * | 2/2010 | Tanuma ............... 15/106 |
| 2011/0146016 | A1 * | 6/2011 | Gatzemeyer et al. ......... 15/167.1 |

FOREIGN PATENT DOCUMENTS

| | | |
|---|---|---|
| JP | 2003501137 | 1/2003 |
| JP | 2006520212 A | 9/2006 |
| JP | 2007263847 A | 10/2007 |
| JP | 2007312259 A | 11/2007 |
| JP | 2009240760 A | 10/2009 |
| WO | 02083257 A1 | 10/2002 |
| WO | 2004073941 A1 | 9/2004 |
| WO | 2006137648 A1 | 12/2006 |
| WO | 2007112112 A1 | 10/2007 |
| WO | 2009034157 A1 | 3/2009 |
| WO | 2009038932 A1 | 3/2009 |

OTHER PUBLICATIONS

Nikkei Technology Online: "Omron Equips Electric Toothbrush With Acceleration Sensor", Jun. 1, 2009, Downloaded from http://techon.nikkeibp.co.jp/english/NEWS_EN/20090601/171041.

* cited by examiner

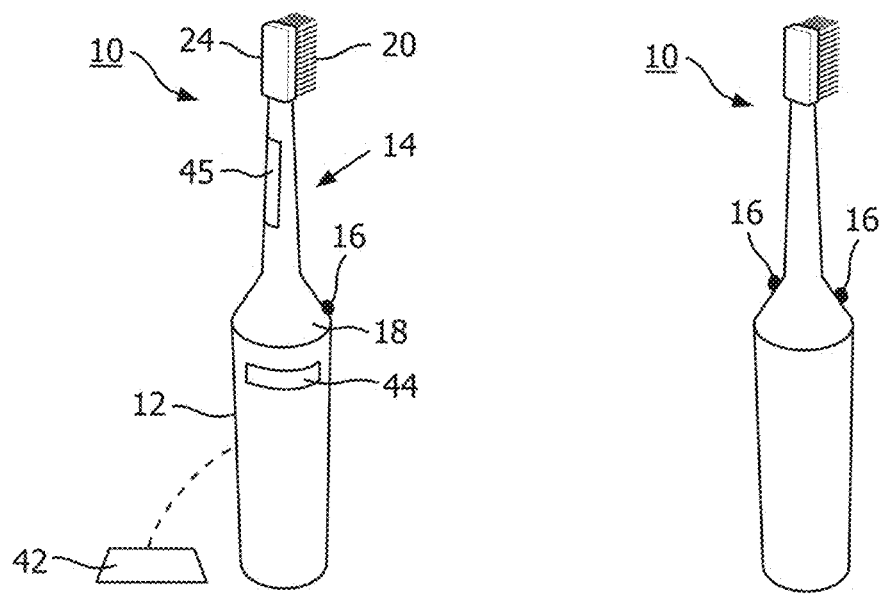

POSITION SENSING TOOTHBRUSH

CROSS-REFERENCE TO PRIOR APPLICATIONS

This application is a divisional of U.S. patent application Ser. No. 14/097,994, filed Dec. 5, 2013, which is a divisional of U.S. patent Ser. No. 13/516,447, filed Jun. 15, 2012, which is the National Stage of International Application No. PCT/IB2010/055333, filed Nov. 22, 2010, which claims the priority of U.S. Provisional Patent Application 61/289,476, filed Dec. 23, 2009, all of which are incorporated herein in whole by reference.

This invention relates generally to toothbrushes, and more specifically concerns the determination of the position of the toothbrush bristles in the mouth, including how far the toothbrush is into the mouth, and whether the user is brushing the inside or outside surfaces of the teeth.

Careful brushing of all the teeth in the mouth is important for good dental health. The teeth in each region of the mouth require careful and complete attention. In order to accomplish this, it is helpful to give feedback to users concerning how long a user brushes in each region of the mouth. This encourages the user to carefully brush all their teeth, spending sufficient time in each region. Previous arrangements for determining time spent in each region have utilized sensors to determine the position of the bristle set. However, such systems have the disadvantage of requiring a reference point or known starting position to determine the position of the bristle set in the mouth of the user, i.e. the position of the bristles relative to the teeth.

Accordingly, it is desirable to provide reliable information back to the user concerning the position of the bristle set in the mouth, preferably with an inexpensive system. This will be helpful in overcoming incomplete brushing habits.

In one embodiment, the toothbrush is capable of sensing the position of the bristle set position and a brushhead portion thereof relative to the tooth and comprises: a toothbrush which includes a handle portion and a brushhead portion with a bristle set at one end thereof for cleaning the teeth of a user; at least one sensor located on said toothbrush such that it is outside the mouth when the bristle set is in position to brush the teeth, the sensor being responsive to temperature, wherein the sensor is oriented such that it detects the temperature of the skin when the bristle set is in a position adjacent one of the outside or inside surfaces of the teeth, and detects the environmental temperature outside the mouth when the bristle set is in a position adjacent the other of the outside or inside surfaces of the teeth; a processor within the toothbrush responsive to the temperature information from the sensor for determining whether the bristle set is in position to brush the outside surfaces or inside surfaces of the teeth; and an indication system responsive to the processor for indicating to the user the position of the bristle set relative to the teeth.

In another embodiment, the toothbrush is capable of sensing the position of the bristle set portion thereof relative to the teeth, and comprises: a toothbrush which includes a handle portion and a brushhead portion, with a bristle set at one end thereof for cleaning the teeth of a user; at least one sensor located on a back member for the bristle set for providing orienting information of the sensor relative to the cheek of the user; a processor responsive to the orienting information to provide an output indicating whether the bristle set is positioned adjacent the outside surfaces of the teeth or the inside surfaces of the teeth; and an indicator system responsive to the processor for indicating to the user whether the bristle set is in position to brush the outside surfaces of the teeth or the inside surfaces of the teeth.

In another embodiment, the toothbrush is capable of sensing how far a toothbrush penetrates into the mouth, and comprises: a toothbrush which includes a handle portion, a neck portion and a bristle set portion at a distal end of the neck portion for cleaning teeth of a user; a plurality of light sources positioned in a sequence along the neck portion of the toothbrush, the light sources oriented such that the relative number of lights within the mouth and outside of the mouth is indicative of the portion of the toothbrush which is in the mouth; and a receiver for receiving light from uncovered light sources outside the mouth, wherein the light sources are differentiated from one another by a selected characteristic, where the receiver includes a system for indicating to the user how far the toothbrush has penetrated into the mouth.

FIGS. 1 and 2 are simple elevational views for a first embodiment of a toothbrush with one and two IR sensors.

Figure 3:
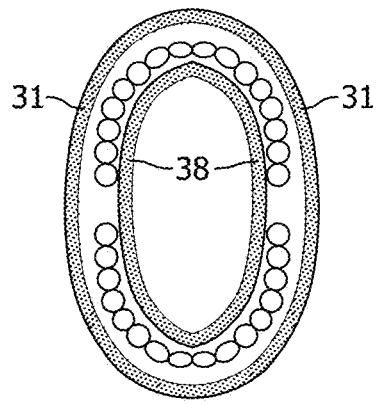
FIGS. 3-6 are simplified diagrams showing brushing coverage relative to a set of teeth.

FIGS. 1-9 illustrate the structure of a first embodiment of the toothbrush described herein and the possible positions of the bristle set portion of the toothbrush in the mouth. Sensors are used on the toothbrush handle, which is outside of the mouth during brushing, to determine the orientation of the bristle set relative to the teeth when the bristle set is in the mouth in particular, whether the bristles are in position for brushing the outside surfaces of the teeth or the inside surfaces of the teeth. In the embodiment of FIGS. 1-9, a toothbrush 10, typically a power toothbrush, which includes a handle portion 12 and a brushhead portion 14, includes at least one sensor 16 near the upper end 18 of handle 12. At the distal end of brushhead 14 is a bristle set 20, fixed to a bristle plate or back member 24. Sensors 16 in the embodiment shown are IR sensors, which are responsive to temperature. FIG. 1 shows an arrangement with a single IR sensor, while FIG. 2 shows two IR sensors, approximately 180° apart. While FIGS. 1 and 2 show the sensors in the toothbrush handle, they could be on the neck of the toothbrush, as long as the sensors remain outside of the mouth.

Figure 7:
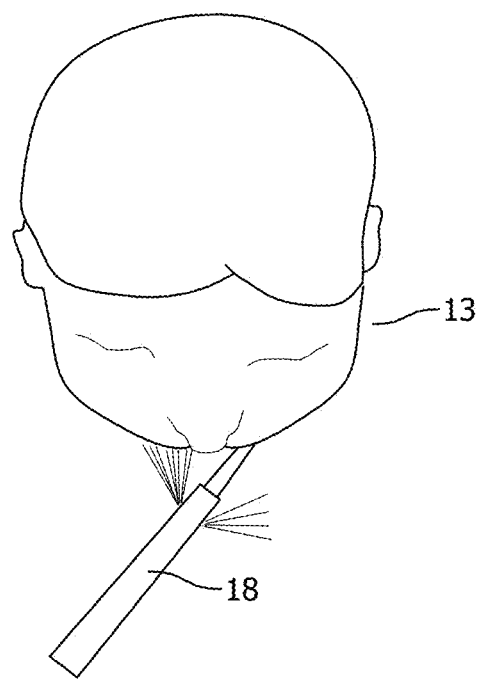
FIGS. 7-9 are illustrations of the position of the toothbrush in a user's mouth and the direction of the IR sensor.
Figure 8:
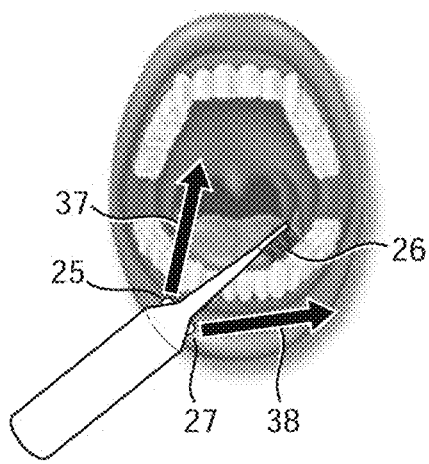
Figure 9:
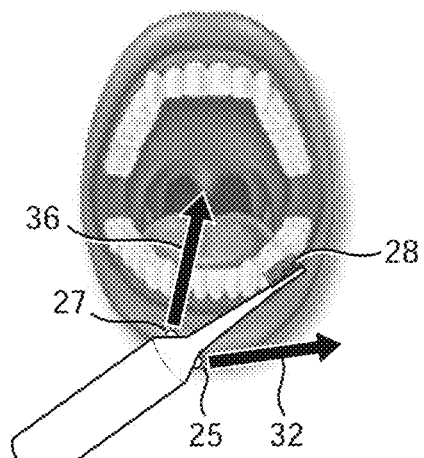

FIG. 7 shows the toothbrush 10 in the mouth of a user 13. FIGS. 8 and 9 show a toothbrush 10 with two sensors 25 and 27 oriented so that when bristles 26 are oriented against the outside surfaces 28 of the teeth (FIG. 9), sensor 25 is pointed away from the skin of the user toward the environment (arrow 32), measuring ambient temperature (72° F.), while the other sensor 27 is pointed toward the skin of the user (arrow 36) and will measure body temperature (98.6° F.). When toothbrush 10 is positioned so that the bristles 25 are oriented against the inside surfaces of the teeth (FIG. 8), sensor 25 will be pointing in the direction of the skin (arrow 37) and sensor 27 will be pointing toward the environment (arrow 38).

It should be understood that only one sensor can be used and still provide effective results, since in one orientation of the toothbrush, the sensor will read 98.6° F., while in the other orientation, the sensor will read the environment temperature, 72° F., for example. In either case, using two sensors or one, the temperature information obtained by the sensor(s) is applied to microprocessor 44 (FIG. 1) within the toothbrush, wherein the microprocessor, having been programmed relative to the temperatures measured by the sensors and the position of the toothbrush, will make a determination of the position of the bristles. It will then send this information to a display device 42, which is typically, but not necessarily, separate from the toothbrush. The display, for instance, could be in a charger assembly for the toothbrush. It could be on a separate display or even on the toothbrush. The system could also provide an audible indication of bristle position. In any event, the system provides an indication to the user of the orientation of the bristles relative to the teeth.

FIGS. 3-6 illustrate the regions of the mouth that can be determined (inside tooth surfaces or outside tooth surfaces) by the arrangement discussed above and shown in FIG. 1 or 2. FIG. 3 shows the combined outside surfaces 37 and inside surfaces 38.

Figure 4:
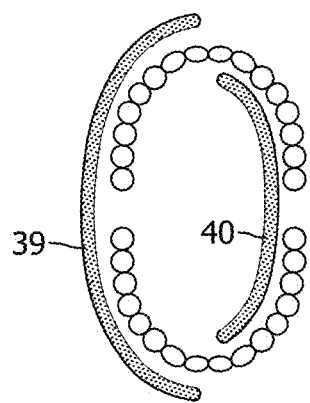
Figure 5:
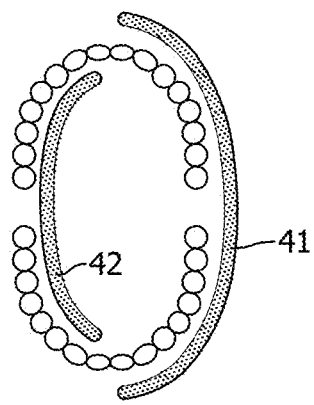
Figure 6:
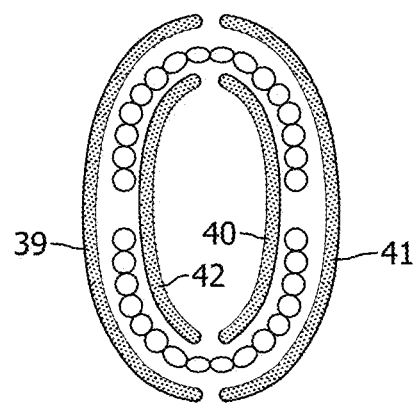

An accelerometer or inclinometer 45 can be added to the toothbrush 10, which, with the sensors, provides an ability of the toothbrush to distinguish four zones in the mouth, in particular, left and right sides of the mouth, and the inside and outside teeth surfaces. FIGS. 4 and 5 illustrate the coverage of a 180° difference in the inclination of the bristles when brushing the regions 39 and 40 (FIG. 4), and regions 41 and 42 (FIG. 5). FIG. 6 illustrates the four zones together.

Further, the chewing surfaces of the teeth can also be identified by means of two additional temperature sensors positioned at approximately 90° to the original two temperature sensors. All of the temperature and accelerometer/inclinometer information is provided to the microprocessor 44, which determines which region of the teeth the bristles are directed toward or against. While IR sensors have been disclosed, other sensors and techniques could be used to detect the presence of the face as approved to the environment. Those could include reflective or triangular IR sensing, capacitive sensing, proximity sensing, or even sonar (acoustic distance sensor) or laser sensing.

Figure 10:
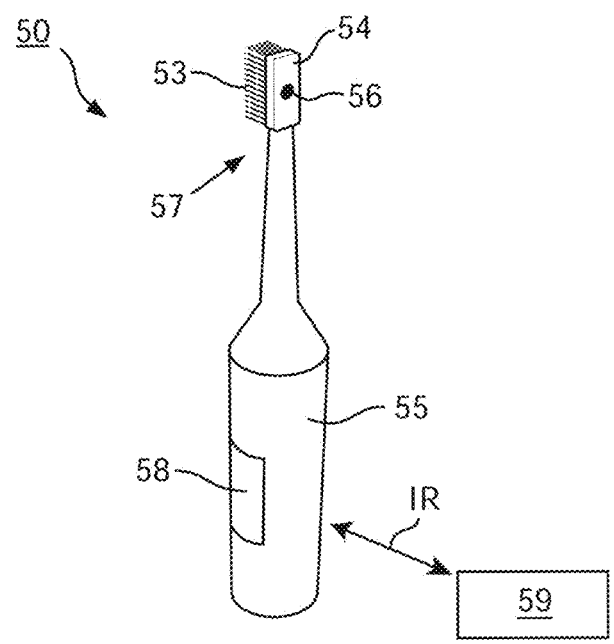
FIG. 10 is an elevational view of one variation of a second embodiment of the position sensor.
Figure 11:
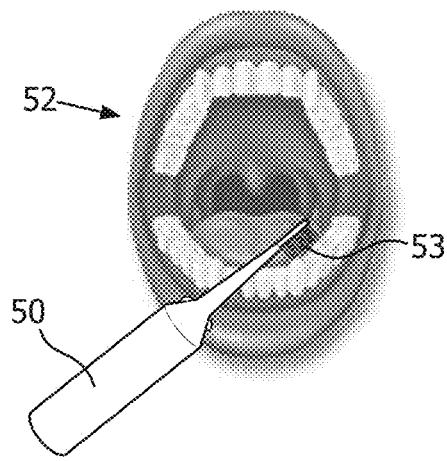
FIGS. 11 and 12 are brushing diagrams for the embodiment of FIG. 10.
Figure 12:
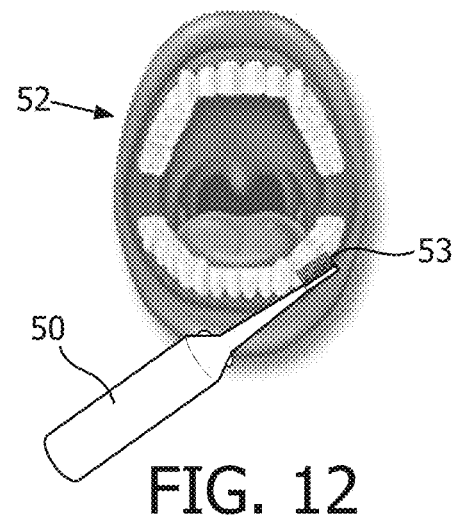

In the particular embodiment and variations thereof FIGS. 10-18, the object again is to determine whether the bristles and the toothbrush are oriented toward the outside or the inside surfaces of the teeth. These variations accomplish the bristle position determination relative to the interior surface of the cheek of the user. In each of the variations, a sensor assembly is positioned on the bristle back plate. When brushing the inside of the teeth, the sensor assembly will face the inside of the mouth away from the cheek, while when brushing the outside surfaces of the teeth, the sensor assembly will face the interior surface of the cheek. The different sensor output between these two positions is processed to provide an indication to the user of the position of the bristles. FIGS. 11 and 12 show a toothbrush 50, with a handle 35 and a brushhead 57, positioned in a user's mouth, shown generally at 52. In FIG. 11, the bristles 53 are positioned against the inside surfaces of the teeth, such that the sensor 56 on the bristle back plate 54 faces the inside of the mouth. In FIG. 12, the toothbrush 50 is oriented so that the bristles 53 are positioned against the exterior surfaces of the teeth. In this position, the sensor 56 faces the cheek of the user.

There are several embodiment variations disclosed herein relative to different sensors suitable for differentiating between the bristles facing the mouth region or facing the cheek of the user. FIG. 10 shows one embodiment variation in which a bristle back plate 54 of the toothbrush 50 is equipped with an infrared temperature sensor 56. When the outside surfaces of the teeth are being brushed, sensor 56 will measure the temperature of the cheek. When brushing the inside surfaces of the teeth, sensor 56 will measure the temperature inside the mouth. Since there is a temperature difference, the two positions of the bristles can be distinguished. The measured temperature values determined by the sensor are provided to a microprocessor illustrated generally at 58 in the toothbrush 55, which is programmed via a look-up table or the like to provide an indication of the position of the bristles to a display 59 which, like the embodiments described above, can be part of a separate unit, such as a charging unit. The information is provided typically by IR (infrared) communication. The display could also be on the toothbrush itself or another display device apart from a charger. It could be visual, audible or other type of indication.

Figure 13:
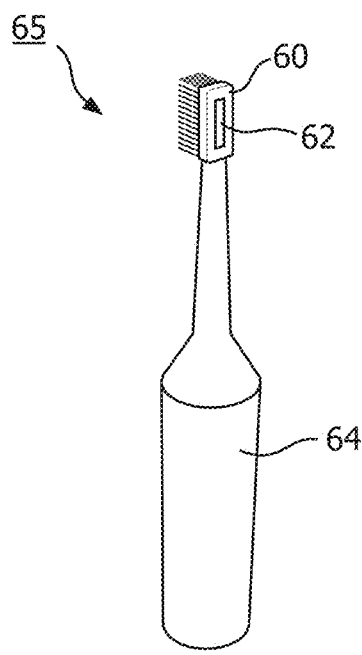
FIGS. 13 and 14 are elevational and top views of a further variation of the second embodiment.
Figure 14:
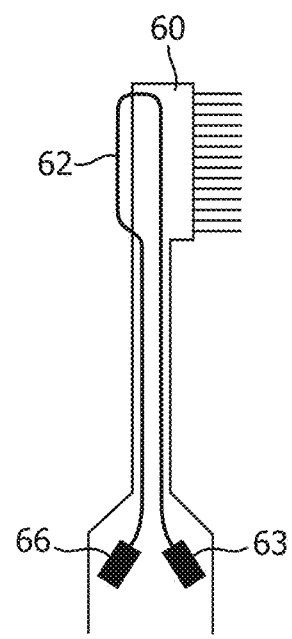

In the variation of FIGS. 13 and 14, bristle back plate 60 is equipped with an optical fiber 62. The fiber 62 extends in a loop from the handle 64 of toothbrush 65 through the back of the bristle set and then back to the handle. At one end of the fiber 62, an LED 63 is mounted that provides light which moves through fiber 62. On the other end of the fiber is a light sensor 66 which measures the intensity of the light coming out of the fiber. When the outside surfaces of the teeth are being brushed, the optical fiber 62 will touch the cheek. Due to this cheek contact, there will be a change of the refractive index at the border of the fiber. Some light will now escape from the fiber and the light intensity sensed by light sensor 66 decreases compared to when the bristles are only adjacent the inside surfaces of the teeth. The sensor provides a different value of light intensity to the toothbrush microprocessor, depending upon whether the inside or outside surfaces of the teeth are being brushed. The microprocessor provides an indication of the position of the bristles to the user through a display or other communication means, as discussed above.

Figure 15:
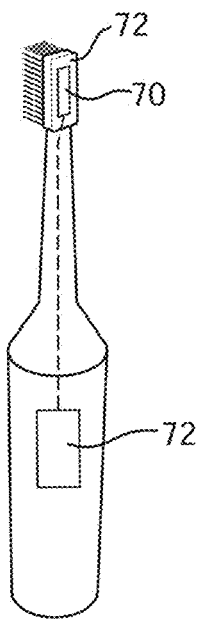
FIG. 15 is an elevational view of another variation of the second embodiment.

FIG. 15 shows another variation, in which a metal plate 70 is mounted at the bristle back plate 72. Plate 70 is covered with a thin layer of plastic. The capacitance of metal plate 70 changes when the metal plate touches the cheek. The capacitance of the plate can be measured by a sensor. When brushing the outside surfaces of the teeth, the capacitance of the plate will be higher due to contact with the cheek. When the inside surfaces of the teeth are being brushed, the capacitance will be lower due to lack of skin contact. The capacitance sensor 72 provides the capacitance values to a microprocessor in the toothbrush, which will then provide an indication to the user of whether the inside or outside surfaces of the teeth are being brushed on a display such as disclosed above.

Figure 16:
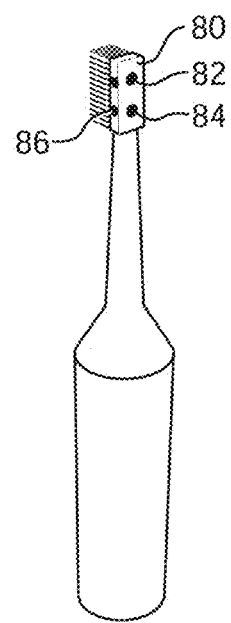
FIG. 16 is an elevational view of a still further variation of the second embodiment.

Still another variation is shown in FIG. 16, wherein the bristle set back plate 80 contains an IR LED 82 and an IR detector 84. The detector 84 detects light that is emitted from the LED. When the back plate of the bristle set is in contact with the cheek, the IR LED 82 and IR detector 84 will be partly covered by the skin of the cheek. The light intensity measured by the detector 84 will be low. When the inside surface of the teeth are being brushed, the light intensity detected by the detector will be higher. The light intensity information is provided to a microprocessor in the toothbrush, which in turn provides an indication to the user of whether the bristles are adjacent the inside or outside surfaces of the teeth. In addition, the sides of the bristle back plate can be equipped with an IR LED and detector combination 86, which will enable detection of additional toothbrush orientations.

Figure 17:
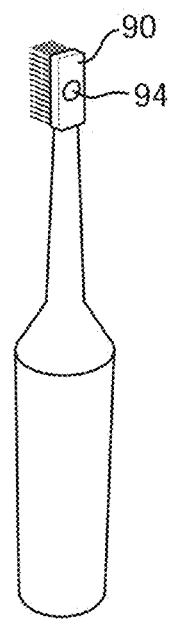
FIG. 17 is an elevational view of yet another variation of the second embodiment.

Another variation is shown in FIG. 17. The bristle back plate 90 contains a contact switch 94. When the outside surfaces of the teeth are being brushed, the bristle back plate will touch the cheek and switch 94 will be triggered, providing an indication of the position of the bristles relative to the teeth. When the inside surfaces of the teeth are being brushed, switch 94 will not be triggered. The signal (or lack thereof) from switch 94 will be processed by a microprocessor and an indication provided to the user of the position of the bristles in the mouth.

Figure 18:
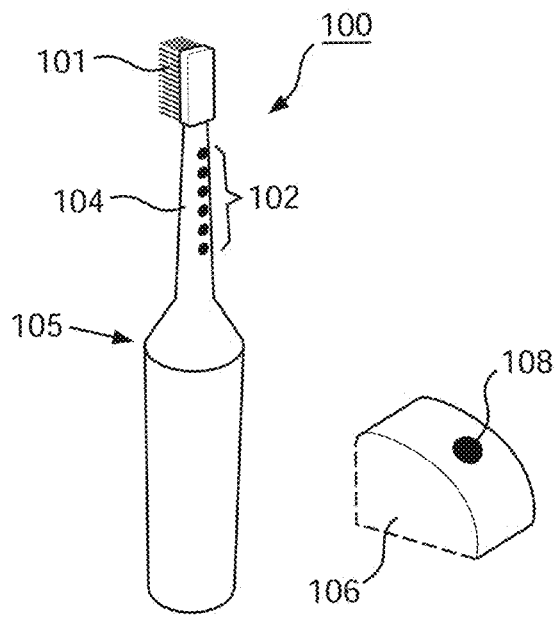
FIG. 18 is a schematic view of a system for determining how far the toothbrush extends into the mouth.

FIG. 18 shows an embodiment which determines how far a toothbrush is inserted into the mouth. The toothbrush 100 is shown with a handle 105, a bristle set 107 and a plurality of LED light sources 102-102 positioned along the neck 104 of the toothbrush. In this embodiment, at least one but preferably two or more LEDs are provided. Each LED has a different emitting characteristic, such as a different frequency. The LEDs produce light which is transmitted to a receiver 106. In operation, as the toothbrush is inserted into the mouth, one or more of the LEDs will be covered, eliminating that characteristic from being transmitted and received by the receiver. The receiver determines the frequencies of light which it receives. That information is provided to a microprocessor, typically in the receiver, which calculates how far the toothbrush is positioned into the mouth. That information is then provided as a display 108, typically on the receiver. The elements on the neck of the toothbrush could also be temperature sensors. In this arrangement, no external light receiver is necessary.

As a variation of the embodiment of FIG. 18, at least four infrared temperature sensors can be provided, with a 3-D accelerometer, in addition to the LEDs (or temperature sensors) on the neck of the toothbrush. The information from the various sensors can then be processed by the microprocessor to determine a specific region of the mouth being brushed.

Hence, several embodiments have been disclosed which provide information to the user concerning the position of the bristles in the mouth relative to the teeth. This allows the user to ensure appropriate brushing of all regions of the teeth.

Although preferred embodiments of the invention have been disclosed for purposes of illustration, it should be understood that various changes, modifications and substitutions may be incorporated in the embodiments without departing from the spirit of the invention, which is defined by the claims which follow.

The invention claimed is:

1. A toothbrush capable of sensing a position of a bristle set portion thereof relative to a user's teeth, comprising:
   a handle portion and a brushhead portion, the brushhead portion having a bristle set at one end thereof for cleaning the user's teeth;
   at least two sensors located on the handle portion of the toothbrush at a location that is outside a user's mouth in response to the bristle set being in position to brush the teeth, the sensors being responsive to a temperature, a first sensor of the at least two sensors further being oriented on the toothbrush such that it detects (i) a temperature of the skin in response to the bristle set being in a position adjacent one of either the outside or inside surfaces of the teeth, and a second sensor of the at least two sensors detects (ii) an environmental temperature outside the mouth in response to the bristle set being in a position adjacent the other of the outside or inside surfaces of the teeth;
   a processor responsive to temperature information from the sensors for determining whether (i) the bristle set is in position to brush the outside surfaces of the teeth or (ii) the bristle set is in a position to brush the inside surfaces of the teeth; and
   an indication system responsive to a bristle set position determined by the processor for indicating the position of the bristle set relative to the teeth.

2. The toothbrush of claim 1, wherein the two sensors are approximately 180° apart on the handle portion.

3. The toothbrush of claim 1, further comprising an accelerometer or inclinometer, wherein information from the accelerometer or inclinometer is provided to the processor, and further wherein the processor determines, in response to the information from the accelerometer or inclinometer, on which side of the mouth the bristle set is located.

4. The toothbrush of claim 1, wherein the sensors are IR (infrared) sensors.

5. The toothbrush of claim 1, further comprising two additional sensors for detecting the toothbrush being present relative to the teeth in an upper or lower jaw of the user.

6. The toothbrush of claim 1, wherein the toothbrush comprises a power toothbrush.

7. The toothbrush of claim 1, wherein the indication system comprises a visual display separate from the toothbrush.

\* \* \* \* \*